(12) United States Patent
Gately

(10) Patent No.: US 9,532,984 B2
(45) Date of Patent: Jan. 3, 2017

(54) THERAPEUTIC COMBINATION FOR CANCER TREATMENT

(75) Inventor: Stephen T. Gately, Scottsdale, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 0 days.

(21) Appl. No.: 14/124,326

(22) PCT Filed: Jun. 11, 2012

(86) PCT No.: PCT/US2012/041924
§ 371 (c)(1),
(2), (4) Date: Dec. 6, 2013

(87) PCT Pub. No.: WO2012/171015
PCT Pub. Date: Dec. 13, 2012

(65) Prior Publication Data
US 2014/0113930 A1    Apr. 24, 2014

Related U.S. Application Data

(60) Provisional application No. 61/495,825, filed on Jun. 10, 2011.

(51) Int. Cl.
*A61K 31/4709* (2006.01)
*A61K 31/473* (2006.01)
*A61K 31/155* (2006.01)
*A61K 31/4706* (2006.01)
*A61K 31/4439* (2006.01)
*A61K 31/519* (2006.01)
*A61K 45/06* (2006.01)

(52) U.S. Cl.
CPC ......... *A61K 31/4709* (2013.01); *A61K 31/155* (2013.01); *A61K 31/4439* (2013.01); *A61K 31/473* (2013.01); *A61K 31/4706* (2013.01); *A61K 31/519* (2013.01); *A61K 45/06* (2013.01)

(58) Field of Classification Search
IPC ................... A61K 31/4709, 31/4439, 31/4706, 31/155, 31/473
See application file for complete search history.

(56) References Cited

U.S. PATENT DOCUMENTS

| 8,263,125 | B2* | 9/2012 | Vaya | A61K 9/2077 424/464 |
|---|---|---|---|---|
| 2003/0216426 | A1* | 11/2003 | Carson et al. | 514/305 |
| 2004/0266834 | A1* | 12/2004 | Copland, III | A61K 31/426 514/342 |
| 2009/0087483 | A1* | 4/2009 | Sison | 424/451 |
| 2010/0285001 | A1 | 11/2010 | Land | |
| 2011/0118298 | A1* | 5/2011 | Fritz et al. | 514/291 |
| 2011/0136821 | A1 | 6/2011 | Claremon | |
| 2012/0220664 | A1* | 8/2012 | Struhl et al. | 514/635 |

FOREIGN PATENT DOCUMENTS

WO    WO 2009/143078    * 11/2009

OTHER PUBLICATIONS

International Search Report, Written Opinion, and Search Strategy for International Application No. PCT/US2012/041924 dated Sep. 4, 2012.

* cited by examiner

*Primary Examiner* — Shirley V Gembeh
(74) *Attorney, Agent, or Firm* — Rodney J. Fuller; Booth Udall Fuller, PLC

(57) ABSTRACT

This invention relates to a synergistic pharmaceutical combination of glucose lowering drugs and autophagy inhibitors, kits containing such combinations, and methods of using such combinations to treat subjects suffering from cancers carrying a specific KRAS mutation. This invention also relates to a theranostic method for cancer treatment.

20 Claims, 1 Drawing Sheet

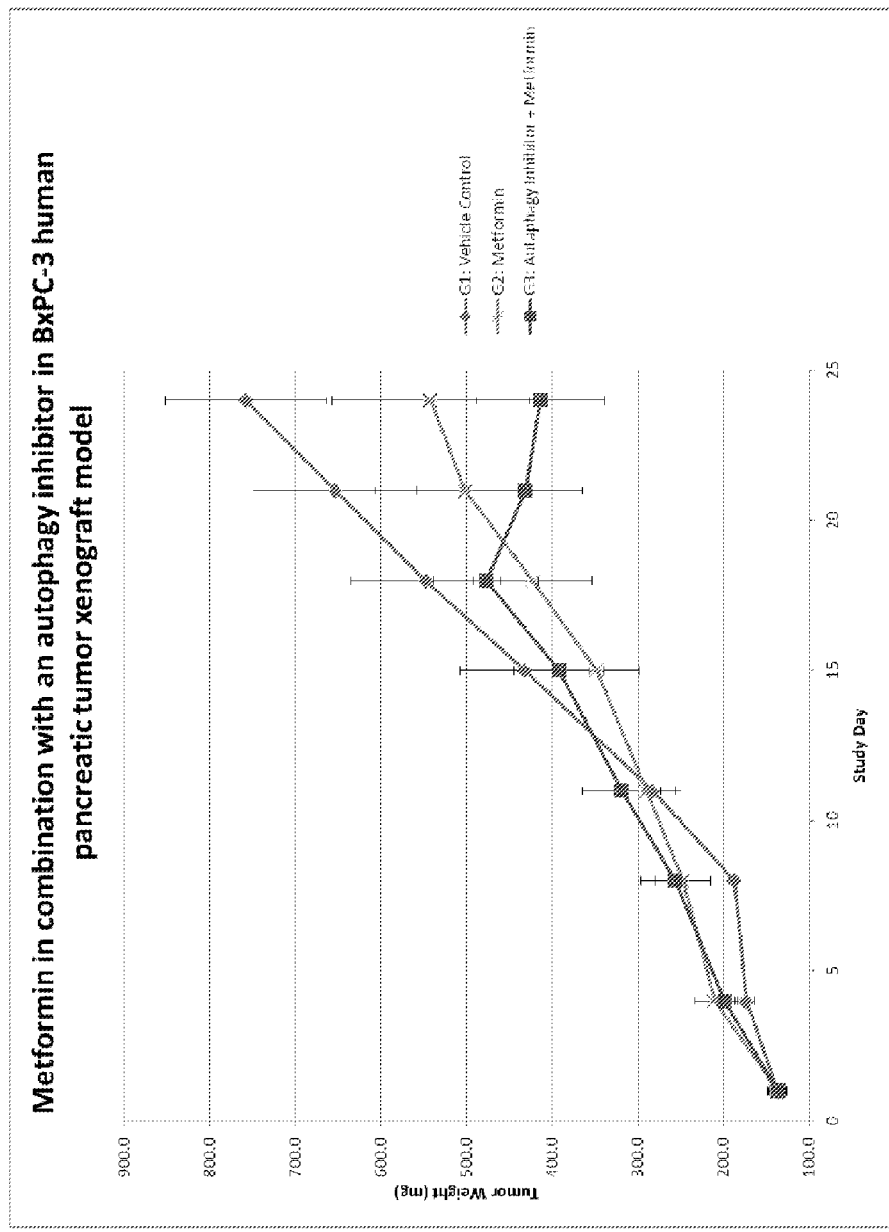

THERAPEUTIC COMBINATION FOR CANCER TREATMENT

CROSS-REFERENCE TO RELATED APPLICATIONS

This application is the national stage of International Patent Application No. PCT/US2012/041924, filed on Jun. 11, 2012, which claims the priority benefit of U.S. provisional application 61/495,825, filed on Jun. 10, 2011, the teachings and content of which are incorporated by reference herein.

INCORPORATION-BY-REFERENCE OF MATERIAL ELECTRONICALLY FILED

Incorporated by reference in its entirety herein is a computer-readable nucleic acid sequence listing submitted concurrently herewith and identified as follows: One 12 kilobyte ASCII (text) file named "110428155sequence_Listing_ST25" created on Dec. 5, 2013.

FIELD OF INVENTION

This invention relates to synergistic pharmaceutical combinations of glucose lowering drugs and autophagy inhibitors, kits containing such combinations, and methods of using such combinations to treat subjects suffering from cancers carrying specific KRAS mutations. In particular, this invention relates to therapeutic combinations of biguanides, thiazolidinediones, dipeptidyl peptidase-4 (DPP-4) inhibitors and antimalarial medications, whereby those additive and synergistic effects are useful in treating subjects suffering from cancers carrying specific KRAS mutations.

BACKGROUND OF THE INVENTION

Cancer cells appear to undergo autophagy in response to oral hypoglycemic agents. Autophagy, or type II programmed cell death, is a catabolic process whereby cells self-digest intracellular organelles. Autophagy is an evolutionarily conserved, genetically controlled process that results in the targeting of cellular proteins and organelles to lysosomes for degradation. Autophagy is a dynamic process and the role of autophagy in cancer is complex and may differ depending on tumor type or context. Autophagy may serve to regulate normal turnover of organelles and to remove those with compromised function to maintain homeostasis. However, autophagy can also be considered a temporary survival mechanism during periods of starvation where self-digestion provides an alternative energy source and also may facilitate the disposal of unfolded proteins under stress conditions. Many agents used to prevent and to treat malaria are inhibitors of autophagy.

One characteristic of cancer cells is they often do not undergo apoptosis. Chemotherapy is used to eliminate these non-apoptotic cells. However, recurrence of cancer subsequent to chemotherapy is observed in some patients. GTPase KRas, also known as V-Ki-ras2 Kirsten rat sarcoma viral oncogene homolog and KRAS, is a protein encoded by the KRAS gene in humans. Like other members of the Ras family, the KRAS protein is a GTPase and is an early player in many signal transduction pathways. KRAS is usually tethered to cell membranes because of its C-terminus isoprenyl group. The protein product of the normal KRAS gene performs an essential function in normal tissue signaling, and the mutation of a KRAS gene is an essential step in the development of many cancers. In particular, cancer cells harboring specific KRAS mutations, for example a glycine to valine substitution at codon 12 (G12V) in K-Ras gene, have been associated with reduced overall survival in many cancers. The transforming protein that results is implicated in various malignancies; nonlimiting examples include lung adenocarcinoma, mucinous adenoma, ductal carcinoma of the pancreas and colorectal carcinoma.

Using colorectal cancer as an example, mutations in KRAS are involved in 22-46% of colorectal carcinogenesis. Mutations in the K-Ras gene, especially a glycine to valine substitution at codon 12 (G12V), have been proposed to be an independent risk factor for reduced overall survival in colorectal cancer patients. The presence of mutations in the K-Ras gene has been associated with the lack of response to anti-EGFR monoclonal antibody treatment. Thus, there is increasing clinical relevance in the detection of mutations in the K-Ras gene with sensitive molecular methods to improve risk stratification and therapeutic strategies.

Patients with Type II diabetes taking oral drugs used to lower blood sugar have a significantly lower incidence of cancer. However, these drugs, i.e., oral hypoglycemic drugs such as buformin, metformin, phenformin and pioglitazone, when used in the treatment of patients with later stage cancers have not shown significant anticancer activity. Therefore, there remains a need to improve and develop new cancer treatments, and to reduce the incidence of recurrence. There remains a need to identify new cancer treatment methods, and new compositions and compounds useful to treat cancer.

SUMMARY OF THE INVENTION

One aspect of this invention provides a pharmaceutical composition comprising: (a) a first compound comprising one or more oral hypoglycemic drugs or pharmaceutically acceptable salts thereof; and (b) a second compound comprising one or more autophagy inhibitors or pharmaceutically acceptable salts thereof. This pharmaceutical composition may further include a pharmaceutically acceptable carrier or excipient. In one embodiment, the first compound, the second compound, and the pharmaceutically acceptable carrier or excipient are formulated together in a single pharmaceutical composition.

In one embodiment of the pharmaceutical composition, the one or more oral hypoglycemic drugs is selected from the group consisting of biguanides, thiazolidinediones, and dipeptidyl peptidase-4 inhibitors (DPP-4). In another embodiment, the one or more oral hypoglycemic drugs is a biguanide selected from the group consisting of buformin, metformin, phenformin, and pharmaceutically acceptable salts thereof. In yet another embodiment, the one or more oral hypoglycemic drugs is a thiazolidinedione selected from the group consisting of pioglitazone, ciglitazone, or troglitazone, rivoglitazone, rosiglitazone, and pharmaceutically acceptable salts thereof. In still another embodiment, the one or more oral hypoglycemic drugs is a DPP-4 inhibitor selected from the group consisting of sitagliptin, vildagliptin, saxagliptin, linagliptin, dutogliptin, gemigliptin, alogliptin, and pharmaceutically acceptable salts thereof.

In one embodiment of the pharmaceutical composition, the second compound is one or more autophagy inhibitors selected from a group consisting of quinacrine, chloroquine, primaquine, mefloquine, artemisinin, 3-methyladenine, hydroxychloroquine, bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels, adenosine, N6-mercaptopurine riboside, wortmannin, vinblastine, antisense that inhibits expression of proteins essential for inducing autophagy and siRNA that inhibits expression of proteins essential for inducing autophagy. In one embodiment, the second compound is the one or more autophagy inhibitors selected from a group consisting of quinacrine, chloroquine, primaquine, mefloquine, artemisinin, and pharmaceutically acceptable salts thereof. In one embodiment, the first compound comprises metformin and pioglitizone; and the second compound comprises mefloquine. In another embodiment, the first compound comprises metformin and pioglitizone; and the second compound comprises mefloquine.

Another aspect of the invention provides a method for achieving a therapeutic effect in a mammal with cancer, comprising the step of administering to the mammal (a) a therapeutically effective amount of a first compound, the first compound comprising one or more oral hypoglycemic drugs or pharmaceutically acceptable salts thereof; and (b) a therapeutically effective amount of a second compound, the second compound comprising one or more autophagy inhibitors or pharmaceutically acceptable salts thereof.

In one embodiment, the first compound and the second compound are administered simultaneously or together in a single pharmaceutical composition comprising a pharmaceutically acceptable carrier or excipient. In another embodiment, the first compound and the second compound are each in a separate pharmaceutical composition comprising a pharmaceutically acceptable carrier, and are administered sequentially. In one embodiment, the one or more oral hypoglycemic drugs is selected from the group consisting of biguanides, thiazolidinediones, and dipeptidyl peptidase-4 inhibitors (DPP-4). In another embodiment, the one or more oral hypoglycemic drugs is a biguanide selected from the group consisting of buformin, metformin, phenformin, and pharmaceutically acceptable salts thereof. In yet another embodiment, the one or more oral hypoglycemic drugs is a thiazolidinedione selected from the group consisting of pioglitazone, ciglitazone, or troglitazone, rivoglitazone, rosiglitazone, and pharmaceutically acceptable salts thereof. In still anther embodiment, the one or more oral hypoglycemic drugs is a DPP-4 inhibitor selected from the group consisting of sitagliptin, vildagliptin, saxagliptin, linagliptin, dutogliptin, gemigliptin, alogliptin, and pharmaceutically acceptable salts thereof.

In one embodiment of the method, the second compound comprises one or more autophagy inhibitors selected from the group consisting of quinacrine, chloroquine, primaquine, mefloquine, artemisinin, 3-methyladenine, hydroxychloroquine, bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels, adenosine, N6-mercaptopurine riboside, wortmannin, vinblastine, antisense that inhibits expression of proteins essential for inducing autophagy and siRNA that inhibits expression of proteins essential for inducing autophagy. In one embodiment, the second compound comprises one or more autophagy inhibitors chosen from quinacrine, chloroquine, primaquine, mefloquine, artemisinin, and pharmaceutically acceptable salts thereof. In another embodiment, the first compound comprises metformin and pioglitizone; and the second compound comprises mefloquine. In one embodiment of the method, the pharmaceutical composition is administered to a mammal with cancer having the mutation G12V in KRAS.

Yet another aspect of the this invention provides a method for achieving a therapeutic effect in a mammal with cancer, and the general method comprises (a) receiving a sample of the mammal; (b) detecting the presence of KRAS G12V mutation; and (c) administering to the mammal having KRAS G12V mutation (i) a therapeutically effective amount of a first compound, the first compound comprising one or more oral hypoglycemic drugs or pharmaceutically acceptable salts thereof; and (ii) a therapeutically effective amount of a second compound, the second compound comprising one or more autophagy inhibitors or pharmaceutically acceptable salts thereof.

Other aspects and iterations of the invention are described in more detail below.

BRIEF DESCRIPTION OF FIGURES

FIG. 1 depicts the tumor growth inhibition by metformin in combination with an autophagy inhibitor in BxPC-3 human pancreatic tumor xenograft mouse model.

DETAILED DESCRIPTION OF THE INVENTION

Oral hypoglycemic agents are widely used in human medicine for the management of non-insulin dependent diabetes mellitus (NIDDM) in patients whose diabetes cannot be managed by diet alone. Oral hypoglycemic agents include biguanides, such as, buformin, metformin, and phenformin; thiazolidinediones, such as, pioglitazone, ciglitazone, troglitazone, rivoglitazone, and rosiglitazone; and DPP-4 inhibitors, such as, sitagliptin, yilaglipti, saxagliptin, linagliptin, dutogliptin, gemigliptin, and alogliptin, which are used for the treatment of Type II diabetes, a disorder involving resistance to secreted insulin. Among these oral hypoglycemic agents, buformin (1-butylbiguanide) is disclosed in U.S. Pat. No. 2,961,377, which is incorporated herein by reference. Buformin is chemically related to metformin and phenformin. Metformin, originally sold as Glucophage™, is now believed to be the most widely prescribed antidiabetic drug in the world; in the United States alone, more than 48 million prescriptions were filled in 2010 for its generic formulations. In addition, pioglitazone is a prescription drug of the class thiazolidinedione (TZD) with hypoglycemic (antihyperglycemic, antidiabetic) action. Pioglitazone is marketed as Actos™, had with sales exceeding $2.4 billion in 2008.

The mechanism by which biguanides cause lactic acidosis is not well understood. It is believed to result from the inhibition of microsomal enzymes involved in glucose metabolism including those involved in gluconeogenesis from lactate and pyruvate and also inhibition of the enzyme pyruvate dehydrogenase which converts pyruvate into acetyl-coenzyme-A. Biguanides reduce elevated blood glucose concentrations in patients with diabetes, but do not increase insulin secretion. There is no blood-glucose-lowering effect in non-diabetic subjects.

One aspect of the present invention provides a method of administering one or more glucose lowering drugs, such as, buformin, metformin, phenformin, pioglitazone, ciglitazone, troglitazone, rivoglitazone, and rosiglitazone, sitagliptin, vildagliptin, saxagliptin, linagliptin, dutogliptin, gemigliptin, and alogliptin, in combination with inhibitors of autophagy. As such, a significant enhancement of anticancer activity, or an additive or synergistic treatment effect can be achieved in cancer cells with a specific mutation in KRAS, G12V. The G12V mutation results in an amino acid substitution at codon 12 in KRAS, from a glycine (G) to a valine (V). Another aspect of the present invention relates to methods of treating individuals who have cancer carrying a KRAS mutation, G12V.

And as used herein, "synergy" or "synergistic" refers to a cooperation or cooperating for an enhanced effect such that the working together of two or more things produces a total effect greater than the sum of their individual effects, as compared to "antagonistic," which is used to especially describe interactions of drugs that counteract or neutralize each other's effect. As used herein, "autophagy inhibitor" is meant to refer to a composition that decreases the level of autophagy in a cell undergoing autophagy in its presence compared to the level of autophagy in a cell undergoing autophagy in its absence.

In some embodiments, the autophagy inhibitor is selected from the group consisting of: quinacrine, chloroquine, primaquine, mefloquine, artemisinin, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels, adenosine, N6-mercaptopurine riboside, wortmannin, and vinblastine. In addition, antisense or siRNA that inhibits expression of proteins essential for autophagy, such as ATG5, may also be used.

As disclosed herein, the anticancer activity of the drug combinations of one or more oral hypoglycemic drugs chosen from buformin, metformin, phenformin, pioglitazone, ciglitazone, troglitazone, rivoglitazone, rosiglitazone, sitagliptin, vildagliptin, saxagliptin, linagliptin, dutogliptin, gemigliptin, and alogliptin, in combination with one or more autophagy inhibitors chosen from quinacrine, chloroquine, primaquine, mefloquine and artemisinin, is enhanced in cells with G12V mutation of KRAS in contrast to the cells that are wild-type for KRAS and cells with a G12D mutation (position 12 in KRAS, from a glycine (G) to an aspartic acid (D)) which demonstrate antagonism to the combination (Table A in Example).

As disclosed herein, another aspect of the invention provides a method of prospective profiling of patients' KRAS status for theranosis. As used herein, the term "theranosis," or "theranostic" refers to the proposed process of diagnostic therapy for individual patients. That is, to test them for possible reactions to taking a new medication and to tailor a treatment for them based on the test results. Similarly, "theranostics" refers to the developments of diagnostic tests that can identify which patients are most suited for a drug and provide feedback on how well the drug is working.

The pharmaceutical compositions or kits of this invention comprise one or more oral hypoglycemic drugs or pharmaceutically acceptable salts thereof, and one or more autophagy inhibitors or pharmaceutically acceptable salts thereof. The one or more oral hypoglycemic drugs is chosen from the group consisting of buformin, metformin, phenformin, pioglitazone, and pharmaceutically acceptable salts thereof; and the one or more autophagy inhibitors is chosen from the group consisting of quinacrine, chloroquine, primaquine, mefloquine, artemisinin, and pharmaceutically acceptable salts thereof.

In any embodiments, hypoglycemic compounds and autophagy inhibitors that are known by those skilled in the art, currently approved for use as pharmaceuticals, or commercially available, may be used as provided in this invention. Additionally, the pharmaceutical composition or compositions may be formulated by one having ordinary skill in the art of delivery in therapeutically effective doses for a chosen mode of administration, as described herein.

In some embodiments, pharmaceutical kits are provided which contain two compounds, a first hypoglycemic compound and a second autophagy inhibitor compound, and instructions for their use in combination. In some embodiments, pharmaceutical kits are provided which contain a first hypoglycemic compound and a second autophagy inhibitor compound that are packaged in separate containers. In some embodiments, pharmaceutical kits are provided which contain a first hypoglycemic compound and a second autophagy inhibitor compound that each is packaged in a unitary container, having separate compartments or sections, such as, a blister pack.

In one embodiment, the pharmaceutical compositions and kits comprise a first compound and a second compound in doses that are therapeutically effective when used in combination. The first compound, one or more oral hypoglycemic drugs, is chosen from buformin, metformin, phenformin, pioglitazone, ciglitazone, troglitazone, rivoglitazone, rosiglitazone, sitagliptin, vildagliptin, saxagliptin, linagliptin, dutogliptin, gemigliptin, alogliptin, and pharmaceutically acceptable salts thereof. The second compound, one or more autophagy inhibitors, is chosen from quinacrine, chloroquine, primaquine, mefloquine, artemisinin, and pharmaceutically acceptable salts thereof. In one embodiment, both compounds are combined and formulated together in a single form of pharmaceutical composition.

The expression "pharmaceutically acceptable salts" includes both pharmaceutically acceptable acid addition salts and pharmaceutically acceptable cationic salts. The expression "pharmaceutically-acceptable cationic salts" is intended to define, but is not limited to, salts such as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define, but is not limited to, salts such as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Other pharmaceutically-acceptable cationic salts of an agent may be readily prepared by reacting the free acid form of the agent with an appropriate base, usually one equivalent in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (e.g., sodium or potassium ethylhexanoate, magnesium oleate) and employing a solvent (e.g., ethyl acetate) from which the desired cationic salt precipitates. The salts may also be isolated by concentrating the reaction solution and/or by adding a non-solvent.

The acid addition salts of an agent may be readily prepared by reacting the free base form of the agent with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when salts such as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

In addition, pharmaceutically acceptable acid addition salts thereof and pharmaceutically acceptable salts thereof may occur as hydrates or solvates. Said hydrates and solvates are also within the scope of the invention.

The pharmaceutical combinations and methods of this invention are all adapted to therapeutic use as agents in the treatment of cancers carrying a KRAS mutation in mammals, particularly humans. In one preferred embodiment, the KRAS mutation is G12V.

The utility of the compounds of the present invention as medical agents in the treatment of cancers carrying a KRAS mutation in mammals (e.g., humans) is demonstrated by the activity of the compounds of this invention in conventional assays as disclosed herein, which can be further demonstrated by animal models and clinical protocol as described below.

The assay reflected in Table A demonstrates the effectiveness of oral hypoglycemic drugs or pharmaceutically acceptable salts thereof and autophagy inhibitors or pharmaceutically acceptable salts thereof in the treatment of cancer carrying a KRAS mutation together by inhibiting cancer cell growth. It also provides a means whereby the activities of the compounds of this invention can be compared between themselves and with the activities of other known compounds. The results of these comparisons are useful for determining dosage levels in mammals, including humans, for the treatment of cancers.

The following dosage amounts and other dosage amounts set forth elsewhere in the specification and in the claims are for an average human subject having a weight of about 65 kg to about 70 kg. The skilled practitioner will readily be able to determine the dosage amount required for a subject whose weight falls outside the 65 kg to 70 kg range, based upon the medical history of the subject and the presence of diseases, e.g., cancers, in the subject. The exact techniques used in determining an effective amount will depend on factors such as the type, physical and/or chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of compound for addition to a cancer cell also includes the determination of an effective therapeutic amount, including the formulation of an effective dose range for use in vivo, including in humans.

Pharmaceutical compositions according to the invention may contain 0.1%-97% of the compound(s) of this invention. In one embodiment of the pharmaceutical composition, a first compound comprises one or more oral hypoglycemic drugs chosen from the group consisting of buformin, metformin, phenformin, pioglitazone, ciglitazone, troglitazone, rivoglitazone, rosiglitazone, sitagliptin, vildagliptin, saxagliptin, linagliptin, dutogliptin, gemigliptin, alogliptin, and pharmaceutically acceptable salts thereof. The embodiment further comprises a second compound comprising one or more autophagy inhibitors chosen from the group consisting of quinacrine, chloroquine, primaquine, mefloquine, artemisinin, and pharmaceutically acceptable salts thereof. In one preferred embodiment of the pharmaceutical composition, the first compound comprises buformin or a pharmaceutically acceptable salt thereof. In another preferred embodiment, the first compound comprises metformin or a pharmaceutically acceptable salt thereof. Yet in another preferred embodiment, the first compound comprises phenformin or a pharmaceutically acceptable salt thereof. In still another preferred embodiment, the first compound comprises pioglitazone or a pharmaceutically acceptable salt thereof. In one preferred embodiment, comprising a first compound that comprises one or more oral hypoglycemic drugs chosen from the group consisting of buformin, metformin, phenformin, pioglitazone, ciglitazone, troglitazone, rivoglitazone, rosiglitazone, sitagliptin, vildagliptin, saxagliptin, linagliptin, dutogliptin, gemigliptin, alogliptin, and pharmaceutically acceptable salts thereof, the embodiment further comprises a second compound comprising quinacrine or a pharmaceutically acceptable salt thereof. In one preferred embodiment comprising one or more oral hypoglycemic drugs chosen from the group consisting of buformin, metformin, phenformin, pioglitazone, ciglitazone, troglitazone, rivoglitazone, rosiglitazone, sitagliptin, vildagliptin, saxagliptin, linagliptin, dutogliptin, gemigliptin, alogliptin, and pharmaceutically acceptable salts thereof, the embodiment further comprises a second compound comprising chloroquine or a pharmaceutically acceptable salt thereof. In one preferred embodiment comprising one or more oral hypoglycemic drugs chosen from the group consisting of buformin, metformin, phenformin, pioglitazone, ciglitazone, troglitazone, rivoglitazone, rosiglitazone, sitagliptin, vildagliptin, saxagliptin, linagliptin, dutogliptin, gemigliptin, alogliptin, and pharmaceutically acceptable salts thereof, the embodiment further comprises a second compound comprising primaquine or a pharmaceutically acceptable salt thereof. In one preferred embodiment comprising one or more oral hypoglycemic drugs chosen from the group consisting of buformin, metformin, phenformin, pioglitazone, ciglitazone, troglitazone, rivoglitazone, rosiglitazone, sitagliptin, vildagliptin, saxagliptin, linagliptin, dutogliptin, gemigliptin, alogliptin, and pharmaceutically acceptable salts thereof, the embodiment further comprises a second compound comprising mefloquine or a pharmaceutically acceptable salt thereof. In one preferred embodiment comprising one or more oral hypoglycemic drugs chosen from the group consisting of buformin, metformin, phenformin, pioglitazone, ciglitazone, troglitazone, rivoglitazone, rosiglitazone, sitagliptin, vildagliptin, saxagliptin, linagliptin, dutogliptin, gemigliptin, alogliptin, and pharmaceutically acceptable salts thereof, the embodiment further comprises a second compound comprising artemisinin or a pharmaceutically acceptable salt thereof. The amount of compounds in such pharmaceutical compositions, therefore, may individually range from about 97%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 3%, or about 1%. In any event, the composition or formulation to be administered will contain a quantity of therapeutic compounds according to the invention in an amount effective to treat the condition or disease of the subject being treated.

Suitable pharmaceutical carriers are described in the most recent edition of Remington's Pharmaceutical Sciences, A.

Osol, a standard reference text in this field. Pharmaceutically acceptable carriers include, but are not limited to, 0.01-0.1M and preferably 0.05 M phosphate buffer or 0.8% saline. Intravenous carriers include fluid and nutrient replenishers, electrolyte replenishers such as those based on Ringer's dextrose, and the like. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media.

A variety of excipients commonly used in pharmaceutical formulations may be selected on the basis of several criteria such as, e.g., the desired dosage form and the release profile properties of the dosage form. Non-limiting examples of suitable excipients include an agent selected from the group consisting of a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combinations of any of these agents.

In one embodiment, the excipient may be a binder. Suitable binders include, for example, starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, peptides, and combinations thereof.

In another embodiment, the excipient may be a filler. Suitable fillers include, for example, carbohydrates, inorganic compounds, and polyvinilpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

The excipient may be a non-effervescent disintegrant. Suitable examples of non-effervescent disintegrants include starches (such as corn starch, potato starch, and the like), pregelatinized and modified starches thereof, sweeteners, clays (such as bentonite), microcrystalline cellulose, alginates, sodium starch glycolate, and gums (such as agar, guar, locust bean, karaya, pecitin, and tragacanth).

In another embodiment, the excipient may be an effervescent disintegrant. By way of non-limiting example, suitable effervescent disintegrants include sodium bicarbonate in combination with citric acid, and sodium bicarbonate in combination with tartaric acid.

The excipient may comprise a preservative. Suitable examples of preservatives include antioxidants (such as alpha-tocopherol or ascorbate) and antimicrobials (such as parabens, chlorobutanol or phenol). In other embodiments, an antioxidant such as butylated hydroxytoluene (BHT) or butylated hydroxyanisole (BHA) may be utilized.

In another embodiment, the excipient may include a diluent. Diluents suitable for use include pharmaceutically acceptable saccharides, such as, sucrose, dextrose, lactose, microcrystalline cellulose, fructose, xylitol, and sorbitol; polyhydric alcohols; starches; pre-manufactured direct compression diluents; and, mixtures of any of the foregoing.

The excipient may include flavoring agents. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot).

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable examples of dispersants include starch, alginic acid, polyvinylpyrrolidones, guar gum, kaolin, bentonite, purified wood cellulose, sodium starch glycolate, isoamorphous silicate, and microcrystalline cellulose.

Depending upon the embodiment, it may be desirable to provide a coloring agent. Suitable examples of color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment.

The excipient may include a taste-masking agent. Examples of taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and combinations thereof.

In various embodiments, the excipient may include a pH modifier. In certain embodiments, the pH modifier may include sodium carbonate or sodium bicarbonate.

The weight fraction of the excipient or combination of excipients in the pharmaceutical composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

The pharmaceutical compositions detailed herein may be manufactured in one or several dosage forms. Suitable dosage forms include transdermal systems or patches. The transdermal system may be a matrix system, a reservoir system, or a system without rate-controlling membranes. Other suitable dosage forms also include tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules; lozenges; a sachet; a sprinkle; a reconstitutable powder or shake; a troche; pellets such as sublingual or buccal pellets; granules; liquids for oral or parenteral administration; suspensions; emulsions; semisolids; or gels.

The dosage forms may be manufactured using conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., prilling, spray drying, pan coating, melt granulation, granulation, wurster coating, tangential coating, top spraying, extruding, coacervation and the like.

Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

Methods of preparing various pharmaceutical compositions with a certain amount of active ingredient are known, or will be apparent in light of this disclosure, to those skilled in this art. For examples, see Remington's Pharmaceutical Sciences, Mack Publishing Company, Easter, Pa., 15th Edition (1975). The pharmaceutical compositions can be prepared using conventional pharmaceutical excipients and compounding techniques. Oral dosage forms may be elixers, syrups, tablets, pills, dragees, capsules, liquids, gels, syrups, slurries, suspensions and the like, for oral ingestion by a patient to be treated. The typical solid carrier may be an inert substance such as lactose, starch, glucose, cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; binding agents, magnesium sterate, dicalcium phosphate, mannitol and the like. A composition in the form of a capsule can be prepared using routine encapsulation procedures. For example, pellets containing the active ingredient can be prepared using standard carrier and then filled into a hard gelatin capsule; alternatively, a dispersion or suspension can be prepared using any suitable pharmaceutical carrier(s), for example, aqueous gums, celluloses, silicates or oils, and the dispersion or suspension then filled into a soft gelatin capsule. Typical liquid oral excipients include ethanol, glycerol, glycerine, non-aqueous solvent, for example, polyethylene glycol, oils, or water with a suspending agent, preservative, flavoring or coloring agent and the like. All excipients may be mixed as needed with disintegrants, diluents, lubricants, and the like using conventional techniques known to those skilled in the art of preparing dosage forms. If desired, disintegrating agents may be added, such as, the cross-linked polyvinylpyrrolidone, agar, or alginic acid or a salt thereof, such as, sodium alginate. If desired, solid dosage forms may be sugar-coated or enteric-coated using standard techniques. For oral liquid preparations, for example, suspensions, elixirs and solutions, suitable carriers, excipients or diluents include water, glycols, oils, alcohols, etc. Additionally, flavoring agents, preservatives, coloring agents and the like may be added.

Since the present invention relates to the treatment of diseases and conditions with a combination of active ingredients that may be administered separately, the invention also relates to combining separate pharmaceutical compositions in kit form. The kit includes two separate pharmaceutical compositions: an oral hypoglycemic drug or a pharmaceutically acceptable salt thereof and an autophagy inhibitor or a pharmaceutically acceptable salt thereof. The kit includes container means for containing the separate compositions such as a divided bottle or a divided foil packet, however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The compounds of the present invention are generally administered in the form of a pharmaceutical composition comprising at least one of the compounds of this invention together with a pharmaceutically acceptable carrier or excipient. Thus, the compounds of this invention can be administered either individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

The combination of this invention may also be administered in a controlled release formulation such as a slow release or a fast release formulation. Such controlled release dosage formulations of the combination of this invention may be prepared using methods well known to those skilled in the art. The method of preferred administration will be determined by the attendant physician or other person skilled in the art after an evaluation of the subject's condition and requirements.

For parenteral administration, the autophagy inhibitor and/or hypoglycemic drugs and or combination formulation thereof can be, for example, formulated as a solution, suspension, emulsion or lyophilized powder in association with a pharmaceutically acceptable parenteral vehicle. Examples of such vehicles are water, saline, Ringer's solution, dextrose solution, 5% human serum albumin, Ringer's dextrose, dextrose and sodium chloride, lactated Ringer's and fixed oils, polyethylene glycol, polyvinyl pyrrolidone, lecithin, arachis oil or sesame oil. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. Parenteral dosage forms may be prepared using water or another sterile carrier. For example, a parenteral composition suitable for administration by injection is prepared by dissolving 1.5% by weight of active ingredient in 0.9% sodium chloride solution. Alternatively, the solution can be lyophilized and then reconstituted with a suitable solvent just prior to administration.

Administering the pharmaceutical composition can be effected or performed using any of the various methods known to those skilled in the art. Systemic formulations include those designed for administration by injection, e.g., subcutaneous, intravenous, intramuscular, intrathecal or intraperitoneal injection, as well as those designed for transdermal, transmucosal, oral or pulmonary administration. For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Injectables are sterile and pyrogen free. Alternatively, the compounds may be in powder form for constitution with a suitable vehicle, e.g., sterile pyrogen-free water, before use. For transmucosal administration, penetrants appropriate to the barrier to be permeated are used in the formulation. Such penetrants are generally known in the art.

For buccal administration, the compounds may take the form of tablets, lozenges, and the like formulated in a conventional manner. The compounds may also be formulated in rectal or vaginal compositions such as suppositories or enemas. A typical suppository formulation comprises a binding and/or lubricating agent such as polymeric glycols, glycerides, gelatins or cocoa butter or other low melting vegetable or synthetic waxes or fats. For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The formulations may also be a depot preparation that can be administered by implantation (for example, subcutaneously or intramuscularly) or by intramuscular injection. In such embodiments, the compounds may be formulated with suitable polymeric or hydrophobic materials (for example, an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various types of sustained-release materials have been established and are well known by those skilled in the art. Sustained-release capsules may, depending on their chemical nature, release the compounds, for example, for a few hours, days, weeks, and up to over 100 days. Depending on the chemical nature and the biological stability of the therapeutic reagent, additional strategies for protein stabilization may be employed.

The compounds used in the invention may also be formulated for parenteral administration by bolus injection or continuous infusion and may be presented in unit dose form, for instance as ampoules, vials, small volume infusions or pre-filled syringes, or in multi-dose containers with an added preservative.

The pharmaceutical compositions described herein may be administered by any means that enables the active agent to reach the agent's site of action in the body of the individual. The dosage administered varies depending upon factors, such as: pharmacodynamic characteristics; its mode and route of administration; age, health, and weight of the recipient; nature and extent of symptoms; kind of concurrent treatment; and frequency of treatment.

The amount of compound administered will be dependent on the activity of the compound in the subject being treated, on the subject's weight, the severity of the affliction, the manner of administration and the judgment of the prescribing physician. In some embodiments, the dosage range would be from about less than 1 to 3000 mg, in particular about 10 to 1000 mg or about 25 to 500 mg, of active ingredient, in some embodiments 1 to 4 times per day, for an average (70 kg) human. Generally, activity of individual compounds used in the invention will vary.

Dosage amounts and intervals may be adjusted individually to provide plasma levels of the compounds that are sufficient to maintain the desired therapeutic effect. Usually, a dosage of the active ingredient can be about 1 microgram to 100 milligrams per kilogram of body weight. In some embodiments a dosage is 0.05 mg to about 200 mg per kilogram of body weight. In another embodiment, the effective dose is a dose sufficient to deliver from about 0.5 mg to about 50 mg. Ordinarily 0.01 to 50 milligrams, and in some embodiments 0.1 to 20 milligrams per kilogram per day given in divided doses per period of time (day, week, month) or in sustained release form is effective to obtain desired results. Therapeutically effective serum levels may be achieved by administering multiple doses, each at set period of time. Treatment for extended periods of time may be recognized to be necessary for effective treatment. In some embodiments, the route may be by oral administration or by intravenous infusion. The amount of active ingredient that is administered to a subject can and will vary depending upon a variety of factors such as the age and overall health of the subject, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

According to some embodiments of the invention, the individual has been diagnosed as having a type of cancer set forth below, and the cancer carries a KRAS mutation G12V. In some embodiments, the individual undergoes surgery and or radiation treatment as part of their therapy. The presence or absence of the G12V mutation can be detected through the use of any process known in the art, including using primers and probes designed according to a specific KRAS allele for PCR, sequencing, hybridization, immunohistochemical analyses.

The National Cancer Institute alphabetical list of cancer includes: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macroglobulinemia; and Wilms' Tumor. The methods of the present invention may be useful to treat such types of cancer.

It should be understood that the invention is not limited to the particular embodiments described herein, but that various changes and modifications may be made without departing from the spirit and scope of this novel concept as defined by the following claims.

EXAMPLES

The following examples are intended to further illustrate and explain the present invention. The invention, therefore, should not be limited to any of the details in these examples.

Example 1

Cancer Cell Growth Inhibition by the Therapeutic Combination

Table A shows the determination of the IC50 (half maximal inhibitory concentration) of the therapeutic combination in vitro in KRAS wildtype cells, in cancer cells carrying mutation G12V, and in cancer cells carrying G12D, by measuring the rate of cell proliferation. Some exemplary primers for detecting G12V and G12D mutations are listed in Table A. An IC50 value is the concentration of an agent needed to inhibit cell growth by 50% relative to the control. The IC50 value needs to be less than 100 µM in order for the compound to be considered further for potential use for treatment. "<20 µM," as shown in Table B, means the IC50 is likely in the nM concentration range. The experiments involved a broad testing of multiple concentrations of metformin, phenformin and pioglitazone against fixed concentrations of the autophagy inhibitors. As shown in Table A, there is an increased sensitivity for the G12V mutation in responding to therapeutic combination of oral hypoglycemic drugs and autophagy inhibitors. Similar tests were carried out in mouse models.

TABLE A

Primers for KRAS Allele Detection:

| Gene Allele | Forward Primer (F)/Reverse Primer (R) | SEQ ID NO. |
|---|---|---|
| KRAS Wildtype | F: 5'-GGTAGTTGGAGCTGGTGGC-3' | 1 |
| | R: 5'-AGAGTGCCTTGACGATACA-3' | 2 |
| G12V | F: 5'-TTGTGGTAGTTGGAGCTGT-3' | 3 |
| | R: 5'-AGAGTGCCTTGACGATACA-3' | 2 |
| G12D | F: 5'-GTGGTAGTTGGAGCTGA-3' | 4 |
| | R: 5'-AGAGTGCCTTGACGATACA-3' | 2 |

TABLE B

Anticancer Activity of Drug Combinations:

| Oral Hypoglycemic Drugs | Autophagy Inhibitor | SW48 KRas | | |
|---|---|---|---|---|
| | | Kras WT | Kras G12V | Kras G12D |
| Metformin | — | 1000 µM | 430 µM | 1300 µM |
| Metformin | Quinicrine 1 µM | 1100 µM | <20 µM | 1100 µM |
| Metformin | Quinicrine 3 µM | 4800 µM | 500 µM | >10000 µM |
| Metformin | Primaquine 1 µM | 100 µM | 80 µM | 100 µM |
| Metformin | Primaquine 3 µM | 2600 µM | 320 µM | >10000 µM |
| Metformin | Mefloquine 1 µM | <20 µM | <20 µM | <20 µM |
| Metformin | Mefloquine 3 µM | 600 µM | 40 µM | 900 µM |
| Phenformin | — | 7.2 µM | 16.2 µM | 10.7 µM |
| Phenformin | Quinicrine 1 µM | 11 µM | 6.5 µM | 23.4 µM |
| Phenformin | Quinicrine 3 µM | 15.8 µM | 4.3 µM | 33.1 µM |
| Phenformin | Chloroquine 1 µM | 23.4 µM | 5.8 µM | 19.5 µM |
| Phenformin | Chloroquine 3 µM | 11.7 µM | 4.5 µM | 16.2 µM |
| Phenformin | Mefloquine 1 µM | 17.2 µM | 1.8 µM | 13.0 µM |
| Pioglitizone | — | 154 µM | >250 µM | 183 µM |
| Pioglitizone | Mefloquine 3 µM | 8.1 µM | 0.4 µM | 9.7 µM |
| Metformin/ Pioglitizone | — | 993 µM | 700 µM | ND |
| Metformin/ Pioglitizone | Mefloquine 3 µM | 965 µM | 100 µM | ND |

ND = Not done

Example 2

Metformin in Combination with an Autophagy Inhibitor Reduced Human Pancreatic Tumor Growth in a Mouse Model A BxPC-3 human pancreatic tumor xenograft mouse model was used to further demonstrate the cancer inhibition effect by the therapeutic combination. BxPC-3 is a human pancreatic cancer cells obtained from the American Type Culture Collection and maintained as recommended. Female mice were inoculated subcutaneously in the right flank with 0.1 ml of a 50% RPMI/50% Matrigel™ (BD Biosciences, Bedford, Mass.) mixture containing a suspension of BxPC-3 human pancreatic tumor cells (approximately $5 \times 10^6$ cells/mouse). RPMI, a bicarbonate buffering system, and Matrigel™, a gelatinous protein mixture, support growth of many types of cultured cells including human normal and neoplastic leukocytes.

When tumors reached approximately 135 mg, mice were randomized into treatment groups. Body weights were recorded when the mice were randomized into groups and were weighted twice per week (on Study Days 3 and 7 for each cycle) thereafter in conjunction with tumor measurements. Group 1 mice were treated with vehicle control containing 5% DMA, 10% propylene glycol, 20% PEG 400, and 65% sterile water. Group 2 mice were treated with metformin only. Group 3 mice were treated with autophagy inhibitor in combination with metformin. Treatment began on the day of randomization. Metformin was delivered orally ad libitum in water. The autophagy inhibitor was delivered daily for 12 days in a vehicle of 5% DMA, 10% propylene glycol, 20% PEG 400, and 65% sterile water. As shown in FIG. 1, during day 1 to day 8, the tumor growth rate in control Group 1 was the lowest one, and Group 2 and Group 3 were similar in tumor growth rate. After day 8, the tumor growth rate in control Group 1 increased dramatically. During day 8 to about day 18, Group 2 treated with metformin had the lowest tumor growth rate, and the Group 1 treated with the vehicle control had the highest tumor growth rate. However, after day 18, the tumor regressed at a fast rate in Group 3 treated with the therapeutic combination. In comparison, the tumor growth in Group 2 continued although at a lower rate than that in Group 1 control. The tumor size regressed nearly 20% by weight within about one week of time in Group 2. Therefore, the autophagy inhibitor and metformin combination had a synergistic and superior treatment effect against human tumor cell growth in vivo.

What is claimed is:

1. A pharmaceutical anticancer composition comprising a synergistic combination of:
   (a) a first compound comprising one or more oral hypoglycemic drugs or pharmaceutically acceptable salts thereof; and
   (b) a second compound comprising one or more autophagy inhibitors or pharmaceutically acceptable salts thereof,
   wherein the one or more hypoglycemic drugs comprise a biguanide selected from the group consisting of metformin and phenformin and the one or more autophagy inhibitors comprise a compound selected from the group consisting of mefloquine and quinacrine, and
   wherein the first compound and the second compound are formulated to independently provide a dosage of 10 mg to 1000 mg.

2. The pharmaceutical anticancer composition of claim 1, further including a pharmaceutically acceptable carrier or excipient, wherein the first compound, the second compound, and the pharmaceutically acceptable carrier or excipient are formulated together in a single pharmaceutical composition.

3. The pharmaceutical anticancer composition of claim 1, wherein the one or more oral hypoglycemic drugs further comprises thiazolidinediones.

4. The pharmaceutical anticancer composition of claim 1, wherein the biguanide is metformin.

5. The pharmaceutical anticancer composition of claim 3, wherein the thiazolidinediones are selected from the group consisting of pioglitazone, ciglitazone, troglitazone, rivoglitazone, rosiglitazone, and pharmaceutically acceptable salts thereof.

6. The pharmaceutical anticancer composition of claim 1, wherein the one or more autophagy inhibitors is mefloquine.

7. The pharmaceutical anticancer composition of claim 1, wherein the one or more autophagy inhibitors is quinacrine.

8. The pharmaceutical anticancer composition of claim 1, wherein the first compound comprises metformin and pioglitizone; and the second compound comprises mefloquine.

9. The pharmaceutical anticancer composition of claim 1, wherein the first compound comprises metformin and the second compound comprises mefloquine, and further wherein, the first compound and the second compound are formulated together in a single pharmaceutical composition.

10. A method for achieving a therapeutic effect in a mammal with cancer, comprising the step of administering to the mammal a therapeutically effective amount of:
(a) a first compound comprising one or more oral hypoglycemic drugs or pharmaceutically acceptable salts thereof; and
(b) a second compound comprising one or more autophagy inhibitors or pharmaceutically acceptable salts thereof,
wherein the one or more hypoglycemic drugs comprise a biguanide selected from the group consisting of metformin and phenformin and the one or more autophagy inhibitors comprise a compound selected from the group consisting of mefloquine and quinacrine, and
wherein the first compound and the second compound are formulated to independently provide a dosage of 10 mg to 1000 mg.

11. The method of claim 10, wherein the first compound and the second compound are administered simultaneously or together in a single pharmaceutical composition further comprising a pharmaceutically acceptable carrier or excipient.

12. The method of claim 10, wherein the first compound and the second compound are each in a separate pharmaceutical composition further comprising a pharmaceutically acceptable carrier, and are administered sequentially.

13. The method of claim 10, wherein the one or more oral hypoglycemic drugs further comprises thiazolidinediones.

14. The method of claim 13, wherein the thiazolidinediones are selected from the group consisting of pioglitazone, ciglitazone, troglitazone, rivoglitazone, rosiglitazone, and pharmaceutically acceptable salts thereof.

15. The method of claim 10, wherein the biguanide is metformin.

16. The method of claim 10, wherein the one or more autophagy inhibitors is mefloquine.

17. The method of claim 10, wherein the one or more autophagy inhibitors is quinacrine.

18. The method of claim 10, wherein the first compound comprises metformin and pioglitazone; and the second compound comprises mefloquine.

19. The method of claim 10, wherein the mammal has cancer having a G12V mutation in KRAS.

20. The method of claim 10, wherein the method further comprises a step of detecting the presence of a KRAS G12V mutation in the mammal prior to the step of administering a therapeutically effective amount of the first compound and a therapeutically effective amount of the second compound.

* * * * *

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Primer for KRAS Allele Detection, synthetic -
      KRAS wildtype Forward

<400> SEQUENCE: 1
ggtagttgga gctggtggc                                              19

<210> SEQ ID NO 2
<211> LENGTH: 19
<212> TYPE: DNA
<213> ORGANISM: Artificial Sequence
<220> FEATURE:
<223> OTHER INFORMATION: Primer for KRAS Allele Detection, synthetic -
      KRAS alleles Reverse

<400> SEQUENCE: 2
agagtgcctt gacgataca                                              19

<210> SEQ ID NO 3
<211> LENGTH: 19
<212> TYPE: DNA
<213> ORGANISM: Artificial Sequence
<220> FEATURE:
<223> OTHER INFORMATION: Primer for KRAS Allele Detection, synthetic -
      KRAS G12V mutation Forward

<400> SEQUENCE: 3
ttgtggtagt tggagctgt                                              19

<210> SEQ ID NO 4
<211> LENGTH: 17
<212> TYPE: DNA
<213> ORGANISM: Artificial Sequence
<220> FEATURE:
<223> OTHER INFORMATION: Primer for KRAS Allele Detection, synthetic -
      KRAS G12D mutation Forward

<400> SEQUENCE: 4
gtggtagttg gagctga                                                17
```